US012564545B2

(12) United States Patent
Godfrey et al.

(10) Patent No.: US 12,564,545 B2
(45) Date of Patent: Mar. 3, 2026

(54) HAIR COLORING COMPOSITIONS COMPRISING 2-AMINO-1-PROPANOL AS ALKALISING AGENTS

(71) Applicant: WELLA GERMANY GMBH, Darmstadt (DE)

(72) Inventors: Simon Godfrey, Darmstadt (DE); Viktoriya Sendyureva, Darmstadt (DE); Teresa Burgahn, Darmstadt (DE); Axel Meyer, Darmstadt (DE); Emad Badali-Baghal, Darmstadt (DE); Bjoern Hoffmann, Darmstadt (DE); John Lankhof, Darmstadt (DE)

(73) Assignee: WELLA GERMANY GMBH, Darmstadt (DE)

(*) Notice: Subject to any disclaimer, the term of this patent is extended or adjusted under 35 U.S.C. 154(b) by 0 days.

(21) Appl. No.: 18/682,414

(22) PCT Filed: Aug. 9, 2022

(86) PCT No.: PCT/EP2022/072358
§ 371 (c)(1),
(2) Date: Feb. 8, 2024

(87) PCT Pub. No.: WO2023/017039
PCT Pub. Date: Feb. 16, 2023

(65) Prior Publication Data
US 2024/0342067 A1 Oct. 17, 2024

Related U.S. Application Data

(60) Provisional application No. 63/230,882, filed on Aug. 9, 2021.

(51) Int. Cl.
*A61Q 5/10* (2006.01)
*A61K 8/22* (2006.01)
*A61K 8/41* (2006.01)

(52) U.S. Cl.
CPC .................. *A61K 8/41* (2013.01); *A61K 8/22* (2013.01); *A61Q 5/10* (2013.01); *A61K 2800/882* (2013.01)

(58) Field of Classification Search
CPC ...... A61K 8/41; A61K 8/22; A61K 2800/882; A61Q 5/10
USPC .............................................................. 8/405
See application file for complete search history.

(56) References Cited

U.S. PATENT DOCUMENTS

| | | | | |
|---|---|---|---|---|
| 5,000,755 | A * | 3/1991 | Anderson | A61Q 5/065 8/405 |
| 5,078,749 | A * | 1/1992 | Anderson | A61K 8/418 564/441 |
| 6,423,101 | B1 | 7/2002 | Yaker et al. | |
| 8,834,580 | B2 | 9/2014 | Goettel et al. | |
| 9,993,406 | B2 * | 6/2018 | Manneck | A61K 8/22 |
| 2005/0050653 | A1 * | 3/2005 | Plos | A61Q 5/10 8/405 |
| 2008/0052841 | A1 | 3/2008 | Cohen et al. | |
| 2009/0158533 | A1 | 6/2009 | Hercouet | |
| 2009/0162309 | A1 | 6/2009 | Hercouet et al. | |
| 2009/0191142 | A1 | 7/2009 | Hercouet et al. | |
| 2010/0154137 | A1 | 6/2010 | Hercouet et al. | |
| 2010/0154141 | A1 | 6/2010 | Hercouet et al. | |
| 2010/0175705 | A1 * | 7/2010 | Hercouet | A61K 8/31 8/406 |
| 2010/0175706 | A1 | 7/2010 | Hercouet et al. | |
| 2010/0178264 | A1 | 7/2010 | Hercouet et al. | |
| 2010/0223739 | A1 * | 9/2010 | Hercouet | A61Q 5/065 8/406 |
| 2012/0210519 | A1 * | 8/2012 | Lim | A61K 8/494 8/409 |
| 2019/0183762 | A1 | 6/2019 | Meyer et al. | |

FOREIGN PATENT DOCUMENTS

| | | | |
|---|---|---|---|
| CN | 106999388 | A | 8/2017 |
| EP | 594811 | A1 | 5/1994 |
| ES | 2570743 | T3 | 5/2016 |
| GB | 1394353 | A | 5/1975 |
| SE | 398967 | B | 1/1978 |
| WO | 98/11863 | A2 | 3/1998 |
| WO | 02/089754 | A1 | 11/2002 |

OTHER PUBLICATIONS

International search report for PCT/EP2022/072358 mailed on Dec. 12, 2022.
Anonymous, "Permanent Hair Color", GNPD09 Apr. 2020 (Apr. 9, 2020), Database accession No. 7534895 Retrieved from the Internet: URL:Mintel XP093004114.

* cited by examiner

*Primary Examiner* — Eisa B Elhilo
(74) *Attorney, Agent, or Firm* — Dennemeyer & Associates LLC

(57) ABSTRACT

The presently claimed invention relates to hair colouring formulations comprising 2-amino-1-Propanol (2A1P/Alanilol) as an alkalizing agent. The compositions of the presently claimed invention provide a series of desirable properties to the user such as a pleasant low chemical odour and a high level of hair bleaching with an acceptable damage profile. The compositions of the presently claimed invention further enable formulators to deliver a wider range of shades or colour formulations by reducing the off-toning adducts of oxidative dyes.

22 Claims, No Drawings

HAIR COLORING COMPOSITIONS COMPRISING 2-AMINO-1-PROPANOL AS ALKALISING AGENTS

CROSS-REFERENCE TO RELATED APPLICATIONS

This is a 35 U.S.C. 371 National Stage Patent Application of International Application No. PCT/EP2022/072358, filed on Aug. 9, 2022, and published as WO/2023/017039 on Feb. 16, 2023, which application claims the benefit of priority to U.S. Application Ser. No. 63/230,882, filed Aug. 9, 2021, all of which are incorporated by reference herein in their entirety.

FIELD OF THE INVENTION

The presently claimed invention relates to oxidative hair colouring compositions comprising 2-amino-1-propanol (Alaninol). The oxidative hair colouring compositions comprising 2-amino-1-propanol provide the combined benefit of delivering broader colour shade palette and improved colour intensity with a low level of hair damage, while ensuring low or no odour levels.

BACKGROUND OF THE INVENTION

Oxidative hair colouring is known since years. Consumers want to be able to colour their hair to many shades, while still having a pleasant and safe usage experience. This requires high lift of hair to deliver a wide range of shades with low or acceptable hair damage while having low or no ammonia smell during the application. In order to deliver a wide range of shades, a large number of dye precursors are used, and they need to be used at sufficient levels to achieve the desired shades.

Ammonia is often used to deliver high lift to obtain a wide variety of dye shades. Delivering high lift causes high damage on hair. Damage of hair includes, e.g., dryness, reduced elasticity, brittleness, split ends, dullness, matte appearance, reduced fullness, rough surface and reduced mechanical strength. Another drawback of the use of ammonia is the heavy smell of ammonia during application.

Monoethanolamine is currently often used within low odour hair colours. It also provides an acceptable level of hair lift and damage. However, it can produce high levels of unwanted dye/alkali adducts which limits the wide range of dye shade formation.

Therefore, there is a need for hair colouring formulations to find an alternative alkali material that provides low odour, and high lift with low or acceptable level of damage, while also giving a low level of formed dye/alkali adducts which enable the formation of a wide range of desired dye shades.

Permanent and demi-permanent oxidative hair colouring products have been used in professional salons and in retail products for use at home for decades. Colouring products typically comprise a tint composition and an oxidizing composition which are packaged separately and mixed immediately before use to form the colouring composition. The tint composition contains so-called oxidative dye precursors which are small molecules (primary dye precursors or coupler dye precursors) and an alkalizing agent, usually ammonia. These primary dyes precursors react with coupler dye precursors in the presence of an oxidizing agent to form larger, coloured dye products within the hair. The oxidizing composition contains the oxidizing agent to enable the colouring process. The oxidizing compositions typically contain a stabilized form of hydrogen peroxide and are sometimes referred to as the developer compositions. The tint composition is thus mixed with the oxidizing composition immediately prior to the application to the hair to be coloured and the resulting mixture of the colouring composition is applied and left on the hair usually for 5 to 50 minutes before rinsing. The mixed colouring composition usually has an alkaline pH between about 8.5 and 10.5.

Oxidative hair colouring compositions comprising ammonia as alkalizing agent within the tint composition are often referred to as permanent hair colourants or "Level 3" hair colourants. Permanent hair colourants are for example marketed under the Koleston Perfect® brand name by Wella Professional in Europe.

Hydrogen peroxide, especially in the presence of ammonia, is capable of bleaching melanin, so that it is possible to obtain shades which are lighter or darker than the natural colour.

Demi-permanent hair colourants, also referred to as "Level 2" colourants, are also typically marketed as two-component systems. They also use primary dye precursors and coupler dye precursors as used in permanent hair colourants but differ in their use of alkalizing agents other than ammonia, in particular monoethanolamine (MEA) or aminomethylpropanol (2-amino-2-methylpropan-1-ol/AMP), and usually function at lower concentrations of hydrogen peroxide, typically 1 to 3 weight % (wt. %) in the mixed colouring composition compared to 3 to 6 or even higher wt. % for permanent "Level 3" colourants. Higher levels of hydrogen peroxide are, however, sometimes used when higher levels of colouring are sought (up to 8 wt. % hydrogen peroxide on the head for some shades). Demi-permanent hair colourants usually cause less melanin bleaching and thus less lift (i.e., removal) of natural hair colour. The resulting dyes may also penetrate less deeply in the hair shaft so that demi-permanent hair colourants can be less long lasting than permanent hair colourants. On the other hand, demi-permanent hair colourants are usually also less damaging to the hair structure than permanent hair colourants and the resulting hair colour may also be more natural looking. A further advantage is that demi-permanent hair colouring compositions do not have the strong ammonia smell of permanent hair colouring compositions and thus have a better consumer experience. A professional brand of demi-permanent hair colourants in Europe is for example Colour Touch® from Wella Professional in Europe. The mixed colouring composition usually has an alkaline pH of between about 8.5 and 10.5.

Ammonia-free hair colouring products have been proposed with the goal to provide colouring results close to those obtained with permanent dyes containing ammonia but without an ammonia odor. For example, Schwarzkopf launched in 2009 in Germany a two-component ammonia-free colourant product under the brand name Essensity®. The alkalizing agent used is MEA and a relatively high level of hydrogen peroxide was used, up to 7.7% within the mixed colouring composition.

L'Oreal launched in 2009 in Western Europe a three-component system for professional usage under the brand name INOA®. The INOA® products comprised a fatty composition, a concentrated dye tint composition and an oxidizing composition to be mixed immediately before use. The fatty composition comprises primarily mineral oil and does not comprise an alkalizing agent. The dye tint composition comprises MEA as alkalizing agent. The three components are recommended to be mixed in a 40:16:60 weight ratio. Subsequently L'Oreal evolved the product into a two-component composition again comprising relatively high levels of a fatty component. Several other L'Oreal publications, e.g.: US 2010/0154141 A1, disclose compositions more or less related to the INOA® products. The non-ammonia alkali is preferably chosen from aminomethylpropanol (AMP or 2-amino-2-methyl-1-propanol) and monoethanolamine. None of these disclosures focuses on delivering a wide variety of dye shades which cannot be obtained either with MEA or AMP.

U.S. Pat. No. 11,219,578 discloses the challenge of obtaining good colour results in MEA based hair colourants and potential for off-toning versus ammonia-based hair colourants. The solution proposed within this patent is to reduce the level of MEA within such compositions. While this overcomes the challenge of the colour result, by reducing the level of MEA, the amount of lift which can be obtained is also reduced. Therefore, while solving one problem, i.e., the off-tone associated with MEA based hair colourants, another problem is created, i.e., the inability to deliver sufficient hair lift.

Although the prior art discloses using two- or three-component systems to obtain a permanent hair colouring result without ammonia, these component systems are based on the use of aminomethylpropanol (AMP or 2-amino-2-methyl-1-propanol) and monoethanolamine. While both species provide an odour benefit and low damage benefit, they both have significant draw backs such as not delivering the desired colour shade palette.

AMP is not effective at providing the bleaching or lift to the melanin within the hair. This prevents products formulated with AMP to deliver a wide range of shades, as lifting, or bleaching the hair is needed to enable shades which are lighter than the consumer or clients base colour, and to provide higher levels of grey coverage. Thus, AMP is not a good replacement for ammonia to deliver a wide range of shades needed for Level 2 and Level 3 hair colourants.

MEA is able to provide better levels of hair lifting and bleaching and is almost at par with ammonia-based systems. However, MEA leads to significant off-tone of some of the oxidative hair dye species used. Color formulation in the presence of MEA can lead to dye structures with the alkali material incorporated into the colored dye product. The dye structures with the alkali incorporated are henceforth referred to as dye adducts. Herein after these dye structures will be named as "mono-dye adducts" or "di-dye adducts". The light absorbing properties of the dye adducts differs from the regular dye species formed in the presence of ammonia, and this is thought to be responsible for the off-tone colour formation observed in the presence of MEA. Differently coloured species are formed concurrently to the desired coloured species. The amount of these dye adducts depends on the choice of primary dye precursor and coupler dye precursor, and the level of MEA and the reaction conditions. A higher level of MEA and a higher pH leads to higher adduct levels.

Thus, formation of mono-dye and/or di-dye can lead to off-tones and prevent the direct reapplication of dye recipes from ammonia colourants into MEA based hair colourants.

There is a need for providing hair colouring compositions that enable the formation of all desired colour shades and intensities and provide high levels of lift, while reducing the level of off-toning adduct species of oxidative dyes and giving a low level of hair damage without the formation of any unpleasant odour during use.

SUMMARY OF THE INVENTION

It is an object of the presently claimed invention to provide hair colouring compositions that enable the formation of all desired colour shades and intensities and provide high levels of lift, while reducing the level of off-toning adduct species and giving a low level of hair damage without the formation of any unpleasant odour during use.

The object has been solved by using 2-amino-1-propanol as an alkalizing agent in an oxidative hair colouring composition.

Accordingly, in one aspect, the presently claimed invention is directed to a hair colouring composition comprising a) 2-amino-1-propanol;
b) at least one oxidizing agent;
c) at least one oxidative primary dye precursor; and
d) at least one oxidative coupler dye precursor.

In one aspect, the presently claimed invention is directed to a hair colouring composition comprising 2-amino-1-propanol in an amount in the range of from ≥1.0 wt. % to ≤10.0 wt. %, based on the total weight of the oxidative hair colouring composition.

In another aspect, the presently claimed invention is directed to a hair colouring composition which is a two-component hair colouring comprising a tint composition (A) and an oxidizing composition (B); wherein the tint composition (A) comprises:

a) 2-amino-1-propanol;
c) at least one oxidative primary dye precursor; and
d) at least one oxidative coupler dye precursor, and wherein the oxidizing composition (B) comprises b) at least one oxidizing agent.

Another aspect of the presently claimed invention relates to a method for colouring hair by applying the oxidative hair colouring composition as described herein above and below.

Another aspect of the presently claimed invention relates to the use of 2-amino-1-propanol as an alkalizing agent for an oxidative hair colouring formulation.

DETAILED DESCRIPTION OF THE INVENTION

The following detailed description is merely exemplary in nature and is not intended to limit the presently claimed invention or the application and uses of the presently claimed invention. Furthermore, there is no intention to be bound by any theory presented in the preceding technical field, background, summary or the following detailed description.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

Furthermore, the terms "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the subject matter described herein are capable of operation in other sequences than described or illustrated herein. In case the terms "(A)", "(B)" and "(C)" or "(a)", "(b)", "(c)", "(d)", "(i)", "(ii)" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

The term "about", when used in relation to a weight ratio or a weight percentage, means that a specific value should be understood as meaning a range of ±10%. For example, the weight proportion of a compound of about 1%, means a weight proportion ranging from 0.9 to 1.1%. For example, the weight proportion of a compound of about 2.5%, means a weight proportion ranging from 2.25 to 2.75%.

In the following passages, different aspects of the subject matter are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "preferred embodiment" means that a particular feature, structure or characteristic described in connection with the embodiment is included in at least one embodiment of the presently claimed invention. Thus, appearances of the phrases "in one embodiment" or "in a preferred embodiment" in various places throughout this specification are not necessarily all referring to the same embodiment but may refer to different embodiments of the presently claimed invention. Furthermore, the features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the subject matter, and form different embodiments, as would be understood by those in the art. For example, in the appended claims, any of the claimed embodiments can be used in any combination.

Furthermore, the ranges defined throughout the specification include the end values as well, i.e. a range of 1 to 10 implies that both 1 and 10 are included in the range. For the avoidance of doubt, the applicant shall be entitled to any equivalents according to applicable law.

For the purposes of the presently claimed invention, '% by weight' or 'wt. %' as used in the presently claimed invention is with respect to the total weight of the colouring composition. Further, the sum of wt. % of all the compounds, as described herein, in the respective components adds up to 100 wt. %. Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

The measurement techniques described hereinabove and herein are well known to a person skilled in the art and therefore do not limit the presently claimed invention.

By "oxidative hair colouring composition", it is meant a ready-to-use composition which can change the colour of hair on which it is applied, and which comprises an alkalizing agent, an oxidizing agent and oxidative dyes.

By "two-component" oxidative hair colouring composition it is meant an oxidative hair colouring composition which is obtained by mixing shortly before use two compositions: a tint composition and an oxidizing composition. The tint composition comprises the oxidative primary dye precursors, oxidative coupler dye precursors and the alkalizing agent. The oxidizing composition comprises the oxidizing agent.

By "composition" it is meant a composition which is mixed by the user with one or more other composition for preparing the ready-to-use oxidative hair colouring composition to be applied to the hair. Hereinafter, the "hair colouring composition" refers to a use/mixed hair colouring composition.

By "user" it is meant the person preparing the hair colouring composition. The user is for example a professional hair stylist working in a salon and is different from the subject on whose hair the composition is applied, or the user is identical to the person on whose hair the composition is applied.

The mixing can take place in a bowl or within a bottle or even through a mixer placed between the stored individual compositions and the point at which it is dispensed to be used. While two component oxidative hair colouring compositions are the most commonly found in the market, there are also others which use three or more components. For example, these colouring compositions comprise a tint composition and a separate alkali composition both of which are mixed in combination with the oxidizing composition to produce the colouring composition. In such a three-component system, the tint composition and the alkali composition are considered to be equivalent to the tint composition of a two-component system.

Alternatively, a tint composition, an anhydrous oxidizer composition and an aqueous composition can be mixed with the anhydrous composition to create the finished mixed colouring composition with the tint composition. In such a three-component system, the anhydrous oxidizer composition and the aqueous composition form the oxidizer composition of the two-component system. An anhydrous dye powder, tablet or granule can also be mixed with an aqueous alkali composition and an oxidizing composition.

Those skilled in the art are aware that there are multiple combinations of the components that can be interchanged to obtain the final mixed hair colouring composition. All these combinations are within the scope of the presently claimed invention which is exemplified in a non-limiting way.

By "lift" (or "lift power") it is meant the amount of lightening caused by the bleaching of the natural hair pigment melanin by using the colouring composition of the presently claimed invention. The amount of lift provided by different hair colouring compositions can be compared by using a human natural dark hair sample (e.g., dark hair of an individual of Chinese descent) and measuring the change of colour achieved following application of the compositions. The change in colour can be measured using well known parameters such as L*a*b* values. A composition can be said to provide a higher lift than another composition, when the resulting L* value or the so-called dL* value (given by $L^*_{final}-L^*_{initial}$) measured for a given treated sample of dark hair is higher for that composition than for the other composition, using the same experimental conditions. The denomination Level 2 (herein used interchangeably with "demi-permanent" or "tone-on-tone") and Level 3 (herein used interchangeably with "permanent") are commonly used in the hair colour trade to differentiate compositions with medium and high lift.

By "oxidizing agent" it is meant an electron accepting compound suitable for use in hair colouring compositions for removing the natural colour of hair (by destroying the melanin pigment) and reacting with oxidative primary dye precursors to enable the reaction with the oxidative coupler dye precursors to form the colour dye products. The most commonly used oxidizing agent in the art is hydrogen peroxide, however further suitable oxidizing agents that can be used in combination with hydrogen peroxide are described below. Oxidizing agents also include those which produce hydrogen peroxide when contacted with water. For example sodium percarbonate, sodium perborate and urea peroxide can be used as anhydrous materials, which when contacted with water release hydrogen peroxide. For such oxidizing agents which product hydrogen peroxide when contacted with water, the wt. % of hydrogen peroxide within mixed colouring composition is considered as the level of b) oxidizing agent.

By "alkalizing agent" it is meant one or more compounds suitable for raising the pH to alkaline level in mixed colouring compositions, in particular to a pH in the range of ≥8.5 to ≤10.5. Generally, the most commonly used alkalizing agents in the art are ammonia and monoethanolamine, however the presently claimed invention involves using an alkalizing agent other than ammonia (herein "non-ammonia, non-monoethanolamine" alkalizing agent), in particular the alkanolamine, 2-amino-1-propanol. The alkali agent is preferably used to raise the pH of the mixed colouring composition to a pH in the range of ≥8.5 to ≤10.5.

The below materials are being used in the embodiments of the presently claimed invention. The presently claimed invention is described with non-limiting embodiments. The listed ingredients are the preferred features as well as other preferred but non-limiting features of the presently claimed invention.

Formulation Chassis and Ingredients

Common ingredients for the hair colouring formulations include, but are not limited to: alkalizers, solvents; water, oxidative dyes; direct dyes; oxidizing agents, hydrogen peroxide; radical scavengers; thickeners and/or rheology modifiers; chelants; pH modifiers and buffering agents; carbonate ion sources; peroxymonocarbonate ion sources; anionic, cationic, non-ionic, amphoteric or zwitterionic surfactants, or mixtures thereof; anionic, cationic, non-ionic, amphoteric or zwitterionic polymers, or mixtures thereof; fragrances; enzymes; dispersing agents; peroxide stabilizing agents; antioxidants; catalysts, natural ingredients, e.g. proteins and protein derivatives, and plant extracts; conditioning agents including silicones and cationic polymers, ceramides, preserving agents, pigments, and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

Examples of formulation chassis for the tint component can be found for example in patent literature or adapted from existing commercial products, especially products comprising non-ammonia alkalizing agents such as from the ColourTouch® range marketed by Wella, INOA® range marketed by L'Oreal or Essensity® range marketed by Schwarzkopf. The components may for example be formulated and delivered as aqueous hair product, emulsion, gel, aerosol, or foam.

The hair colouring compositions of the presently claimed invention preferably further comprises any usual hair colouring chassis ingredients and use any common ingredients, known in the field as long as they are compatible with the requirements set in the claims.

Alkalizing Agent

The hair colouring composition of the presently claimed invention comprises 2-amino-1-propanol as alkalising agent.

In another embodiment of the presently claimed invention, the ready to use composition preferably comprises a second alkalizing agent selected from the group consisting of 2-amino-1-butanol (2A1B), monoethanolamine and ammonia in combination with 2-amino-1-propanol. 2-Amino-1-butanol, monoethanolamine and/or ammonia are preferably present in the same composition as 2-amino-1-propanol, or they are preferably present in a separate composition which is mixed along with the oxidizing composition to create the colouring composition.

In a preferred embodiment, the oxidative hair colouring composition contains ammonia to 2-amino-1-propanol in a molar ratio in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.

In a preferred embodiment, the oxidative hair colouring composition contains monoethanolamine to 2-amino-1-propanol in a molar ratio in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.

In a preferred embodiment, the oxidative hair colouring composition contains 2-amino-1-butanol to 2-amino-1-propanol in a molar ratio is in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.

Oxidizing Agent

The oxidizing agents are preferably water-soluble inorganic peroxide materials which are capable of yielding hydrogen peroxide in an aqueous solution.

In one embodiment of the presently claimed invention, the oxidizing are selected from the group consisting of hydrogen peroxide, inorganic alkali metal peroxides (such as sodium periodate and sodium peroxide), organic peroxides (such as urea peroxide, melamine peroxide), inorganic perhydrate salt bleaching compounds (such as the alkali metal salts of perborates, percarbonates, perphosphates, persilicates, persulphates), and mixtures thereof; preferably from the group consisting of hydrogen peroxide, persulphates, and mixtures thereof; most preferably the oxidizing agent is hydrogen peroxide.

"Water-soluble," as defined herein, means that in standard condition at least 0.1 g, 1 g, or 10 g of the oxidizing agent can be dissolved in 1 litre of deionized water.

In one embodiment, the component b) is preferably present in an amount in the range of ≥1.0 wt. % to ≤8.0 wt. %, more preferably in an amount in the range from of ≥1.0 wt. % to ≤6.0 wt. %, more preferably in an amount in the range from of ≥1.2 wt. % to ≤5.0 wt. %, based on the total weight of the oxidative hair colouring composition.

The oxidizing agents can be provided in aqueous solution or as a powder which is dissolved prior to use.

Oxidative Primary Dye Precursors

In one embodiment of the presently claimed invention, the oxidative primary dye precursors are selected from of the group consisting of toluene-2,5-diamine, p-phenylenediamine, n-phenyl-p-phenylenediamine, N,N-bis(2-hydroxyethyl)-p-phenylenediamine, hydroxyethyl-p-phenylenediamine sulphate, hydroxypropyl bis(n-hydroxyethyl-p-phenylenediamine), 2-methoxymethyl-p-phenylenediamine, 2-chloro-p-phenylenediamine, p-aminophenol, p-methylaminophenol, 4-amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol 2,3-diaminodihydroxypyrazolopyrazolone dimethosulfonate, 4,5-diamino-1-hexylpyrazol, hydroxypropyl-p-phenylenediamine, dimethylpiperazinium aminopyrazolopyridine chloride hydrochloride, methylimidazoliumpropyl p-phenylenediamine, hydroxyethoxy aminopyrazolopyridine and salts thereof.

Oxidative Coupler Dye Precursors

In one embodiment of the presently claimed invention, the oxidative coupler dye precursors are selected from the group consisting of resorcinol, 4-chlororesorcinol, 2-chlororesorcinol, 2-methylresorcinol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, hydroxybenzomorpholine, 2-amino-5-ethylphenol, 6-amino-m-cresol, 6-amino-o-cresol, 2,4-diaminophenoxyethanol, 2-amino-4-hydroxyethylaminoanisole, 1,3-bis-(2,4-diaminophenoxy)propane, 2,6-dihydroxyethylaminotoluenep, m-phenylenediamine, 2,4-diamino-1,5-di(2-hydroxyethoxybenzene, 1-naphthol, 2-methyl-1-naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindole, 6-hydroxyindole, dihydroxyindoline, phenyl methyl pyrazolone, 1,2,4-trihydroxybenzene, 5-((2-hydroxyethyl)amino)-1,3-benzodioxol, isatin, hydroquinone, 4-formyl-1-methylquinolinium-p-toluenesulfonate and salts thereof.

These and other primary dye precursors and coupler dye precursors may be used in different combination to achieve the nuance sought, as is known in the art.

Direct Dyes

Direct dyes may also be incorporated in any of components of the presently claimed invention, in particular in the tint composition. The compositions of the presently claimed invention may also comprise compatible direct dyes, in an amount that is sufficient to provide additional colouring, particularly with regard to intensity. Typically, such an amount will range from 0.005% wt. % to 4.0 wt. %, based on the total weight of the composition. When the composition is obtained by mixing a tint composition and an oxidizing composition, the direct dyes are usually incorporated in the tint composition.

In one embodiment of the presently claimed invention, direct dyes are selected from the group consisting of Acid Yellow 1, Disperse Red 17, Basic Brown 17, Acid Yellow 9, Pigment Red 49, Acid Yellow 11, Acid Black 1, 4-Nitro-1,2-phenylenediamine, Picramic acid, HC Red 13, N,N'-Bis(2-hydroxyethyl)-2-nitro-p-phenylenediamine, HC Yellow 5, HC Red 7, HC Blue 2, HC Yellow 4, HC Yellow 3, HC Blue 1, HC Yellow 2, HC Orange 1, HC Red 1, HC Red 3, 4-Amino-3-nitrophenol, 2-Hydroxyethylamino-5-nitroanisole, 3-Nitro-p-hydroxyethylaminophenol, 3-Methylamino-4-nitrophenoxyethanol, 2-Nitro-5-glyceryl methylaniline, HC Violet 1, HC Orange 2, HC Orange 3, HC Yellow 9, 4-Nitrophenyl aminoethylurea, HC Red 10, HC Red 11, 2-Hydroxyethyl picramic acid, HC Blue 12, HC Yellow 6, Hydroxyethyl-2-nitro-p-toluidine, HC Yellow 12, HC Blue 11, HC Blue 10, HC Blue 6, HC Yellow 7, HC Yellow 10, HC Blue 9, HC Blue 13, 2-Chloro-6-(ethylamino)-4-nitrophenol, 6-Nitro-2,5-pyridinediamine, HC Violet 2, 2-Amino-6-Chloro-4-Nitrophenol, 4-Hydroxypropylamino-3-nitrophenol, Acid Blue 7, HC Yellow 13, HC Red 14, HC Yellow 15, HC Yellow 14, 2,6-Diamino-3-((pyridin-3-yl)azo)pyridine, Basic Orange 69, HC Red 16, Basic violet 2, Basic Red 51, Basic Yellow 87, Basic Orange 31, HC Blue 16, HC red 17, HC Yellow 17, HC blue 18, HC Yellow 16, HC Red 18, HC Orange 6, Basic Orange 1, Basic Red 76, Basic Brown 16, Basic Yellow 57, CI14700, Acid Red 14, Acid Orange 7, Acid Red 88, FD&C Yellow 6, Acid Red 27, Acid Orange 10, Acid Red 33, Acid red 155, Acid Yellow 23, Food Black 2, CI 28440, HC Brown 2, Acid Blue 1, Acid Blue 3, Acid Blue 9, Acid Violet 49, CI 42735, Basic Blue 26, Acid violet 9, Acid Red 92, Acid Yellow 3, Beta-Carotene, CI 50420, Basic Blue 99, 1-Amino-4-hydroxy-9,10-anthracendion, CI 60725, Acid violet 43, Disperse Violet 1, Acid blue 62, Copper phthalocyanine, Carbon black, Disperse Black 9, Lycopene, Hydroxyanthraquinoneaminopropyl methyl morpholinium methosulfate, HC Blue 8, HC Green 1, Curry red, 2-Hydroxy-1,4-naphthoquinone, CI 77289, Solvent Green 7*, Lawsonia inermis* Cera, CI 73000, *Indigofera tinctoria*, Carmines, HC Blue 14, Acid Red 18, CI 42053, Acid Red 52, Acid Green 25, Disperse Blue 377, Pigment Red 57, HC Blue 15, Tetrabromphenol Blue, Cationic Blue 347, Bromthymol blue sodium, Anthocyanins, Chlorophyllin-Copper complex, Annatto, Natural Green 3, Betanin, Capsanthin, Basic Yellow 29 and combinations thereof.

Chelants

Chelants are preferably used prior to application of a hair colouring composition to remove and/or bind metal ions which are bonded to hair. For example, U.S. Pat. No. 5,635,167 discloses a process for the removal of exogenous metal ions that are attached to hair. The treatment comprises contacting hair with a blend of chelating agents (selected from the group consisting of amino acid chelating agents, polyphosphate chelating agents and phosphonate chelating agents) at a pH of between 4 and 9 and at a concentration of between 4% to 25% by weight prior to colouring.

As already disclosed in WO 02/089754, among the usual ingredients encountered within a hair colouring composition, the presence of a chelant such as EDTA or EDDS and their salts thereof may be beneficial in several ways, as chelants can reduce hair damage caused by oxidizing agents.

Chelants, especially disodium EDTA, are also commonly used as stabilizer in the oxidizing component. Besides EDDS and EDTA, any other chelants can be used in the presently claimed invention, such as; diethylenetriamine penta(methylene phosphonic acid) DTPMP, methylglycinediacetic acid trisodium salt (MGDA), 1-hydroxyethylidene-1,1-diphosphonic acid (HEDP), EDDG, HPDDS and EDDHA and their salts thereof.

In a further embodiment of the presently claimed invention, the at least one chelant is selected from the group consisting of ethylenediamine tetraacetic acid (EDTA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), salts thereof, derivatives thereof, and mixtures thereof.

In one embodiment of the presently claimed invention, the chelant is EDDS, more preferably is (S,S)-EDDS and their salts thereof.

In a further embodiment of the presently claimed invention, the hair colouring composition comprises at least one chelant in an amount in the range from ≥0.20 wt. % to ≤1.5 wt. %, based on the total weight of the oxidative hair colouring composition.

Fatty Substances

In one embodiment of the presently claimed invention, the hair colouring composition preferably comprises at least one fatty substance that does not contain any free carboxylic acid groups, i.e. free of —C(═O)—OH groups and —C(═O)—$O^-$. The term "fatty substance" means an organic compound that is insoluble in water at room temperature (25° C.) and at atmospheric pressure (15 mg/L water, preferably ≤5 mg/L water). In addition, under the same temperature and pressure conditions, the fatty substances are soluble in organic solvents such as chloroform, ethanol or benzene.

In a preferred embodiment of the presently claimed invention, the fatty substances are selected from the group consisting of liquid hydrocarbons, non-silicone oils of animal, plant, mineral or synthetic origin, fatty alcohols, fatty acids, fatty acid esters and/or fatty alcohol esters, non-silicone waxes, and silicones or mixtures thereof.

More particularly, the liquid hydrocarbons are selected from the group consisting of:

- linear or branched, optionally cyclic, C6-C16 alkanes such as hexane, undecane, dodecane, tridecane, and isoparaffins, such as isohexadecane, isododecane and isodecane,
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

In a preferred embodiment of the presently claimed invention, the liquid hydrocarbons are selected from the group consisting of volatile or non-volatile liquid paraffins, and liquid petroleum jelly.

The compositions of the presently claimed invention preferably comprises an amount of fatty substances that do not contain any free carboxylic acid groups of ≥2 wt. %, more preferably ≤10 wt. %, even more preferably ≤20 wt. %, most preferably ≥30 wt. %, based on the total weight of the hair colouring composition.

In a further embodiment of the presently claimed invention, the hair colouring composition comprises fatty substances in an amount in the range from ≥2.0 wt. % to ≤70.0 wt. %, based on the total weight of the oxidative hair colouring composition.

Fatty Alcohol

In one embodiment of the presently claimed invention, a creamy carrier for the tint composition (A) preferably comprises from ≥10.0 wt. % to ≤30 wt. % of at least one fatty alcohol with 10 to 24 carbon atoms; and/or one or more of ≥0.2 wt. % to ≤6.0 wt. % of at least one diester of formula: $R^1$—CO—O—(CH2-CH2-O)$_n$-CO—$R^2$, where n is 1, 2 or 3, and R1 and R2 are the same or different alkyl radicals with 12 to 20 carbon atoms; and/or one or more of ≥0.5 wt. % glycerine fatty acid ester with 10 to 24 carbon atoms; and/or one or more of ≥0.1 wt. % to ≤10 wt. % of non-ionic and/or anionic and/or ampholytic emulsifiers, based on the total weight of the tint composition.

Lower levels of fatty alcohol can also be used in this chassis, if a less thick composition is desired, for example a level of from ≥2.0% wt. % to ≤10 wt. % of at least one fatty alcohol with 10 to 24 carbon atoms can be used.

The formulations disclosed in WO 98/11863A2 may also be used as a reference for the presently claimed invention. The formulations disclosed in this reference document contain a beeswax-protein hydrolysate- and/or amino acid association, which however may or may not be present in the tint component of the presently claimed invention.

In one embodiment of the presently claimed invention, the hair colouring composition may be a three-component system, as exemplified in US 2010/0223739 A2, in which case the aqueous cosmetic composition comprising at least one fatty substance and at least one surfactant as defined in this document may be considered as a third composition.

Surfactants

In one embodiment of the presently claimed invention, the hair colouring composition comprises at least one surfactant. The at least one surfactant is preferably anionic, cationic or non-ionic. The at least one surfactant is preferably a non-ionic surfactant which is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

Thickeners

The colouring compositions of the presently claimed invention preferably comprises a thickener, in particular a polymeric thickener in an amount that is sufficient to impart a viscosity to the composition that allows for its ready application to hair without unduly dripping off the hair, as is known in the art. Typically, such an amount will be at least about 0.1 wt. %, in some embodiments, at least about 0.5 wt. %, in other embodiments, at least about 1.0 wt. %, based on the total weight of the colouring composition.

Examples of commonly used associative polymeric thickeners are sold under the tradename Aculyn-22 and Aculyn-33 by the company Rohm & Haas, Permulen TR1, Carbopol 2020, Carbopol Ultrez-21 by the company Noveon, and Structure 2001 and Structure 3001 by the company National Starch. Other suitable polymers include polyether polyurethanes, for example Aculyn-44 and Aculyn-46 by the company Rohm and Haas. Another suitable associative polymer is cellulose modified with groups comprising at least one C8-C30 fatty chain, such as the product Natrosol Plus Grade 330 CS sold by the company Aqualon.

In one embodiment of the presently claimed invention the hair colouring composition comprises salt tolerant thickeners, including but not limited to: xanthan, guar, hydroxypropyl guar, scleroglucan, methyl cellulose, ethyl cellulose (available as AQUACOTE®, hydroxyethyl cellulose (NATROSOL®), carboxymethyl cellulose, hydroxypropylmethyl cellulose, microcrystalline cellulose, hydroxybutylmethyl cellulose, hydroxypropyl cellulose (available as KLUCEL®), hydroxyethyl ethyl cellulose, cetyl hydroxyethyl cellulose (available as NATROSOL® Plus 330), N-vinylpyrrolidone (available as POVIDONE®), Acrylates/Ceteth-20 Itaconate Copolymer (available as STRUCTURE® 3001), hydroxypropyl starch phosphate (available as STRUCTURE® ZEA), polyethoxylated urethanes or polycarbamyl polyglycol ester (e.g. PEG-150/Decyl/SMDI copolymer (e.g. ACULYN® 44), PEG-150/Stearyl/SMDI copolymer (available as ACULYN® 46), trihydroxystearin (available as THIXCIN®), acrylates copolymer (e.g. available as ACULYN® 33) or hydrophobically modified acrylate copolymers (e.g. Acrylates/Steareth-20 Methacrylate Copolymer (available as ACULYN® 22), acrylates/steareth-20 methacrylate crosspolymer (available as ACULYN® 88), acrylates/vinyl neodecanoate crosspolymer (available as ACULYN® 38), acrylates/beheneth-25 methacrylate copolymer (available as ACULYN® 28), acrylates/C 10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain.

In one embodiment of the presently claimed invention, the hair colouring composition comprises at least one mineral thickener selected from organophilic clays, fumed silicas, or mixtures thereof. The at least one mineral thickener is present in an amount ranging from ≥1.0 to ≤30 wt. %, based on the total weight of the colouring composition.

In one embodiment of the presently claimed invention, the organic thickener is selected from cellulose-based thickeners (hydroxyethycellulose, hydroxypropyl cellulose, carboxymethylcellulose), guar gum and derivatives thereof (hydroxypropyl guar), gums of microbial origin (xanthan gum, scleroglucan gum), crosslinked homopolymers of acrylic acid or of acrylamido-propanesulfonic acid, and cellulose-based thickeners, such as hydroxyethylcellulose. The at least one organic thickener is present in an amount ranging from ≥0.1 to ≤20 wt. %, based on the total weight of the colouring composition.

Gel Network Thickener System

In one embodiment of the presently claimed invention, the hair colouring composition preferably comprises a gel network thickener system. The gel network thickener system is typically provided in the tint composition and subsequently mixed with the oxidizing composition whilst retaining the gel like network system in the resultant mixed colouring composition. Such gel network thickener systems comprise a surfactant and a fatty alcohol.

In one embodiment of the presently claimed invention, the gel network system preferably comprises a linear or branched C14 to C30 fatty alcohol, preferably selected from the group consisting of cetyl alcohol, stearyl alcohol, cetostearyl alcohol or behenyl alcohols or mixtures thereof. According to the presently claimed invention the tint composition preferably comprises from ≥1.0 wt. % to ≤18.0 wt. %, more preferably from ≤2.0 wt. % to ≤12.0 wt. % of fatty alcohol.

In one embodiment of the presently claimed invention, the gel network system preferably comprises an ionic, cationic or non-ionic surfactant or amphophile.

The gel network thickener system preferably comprises at least one anionic surfactant selected from C8 to C30 alkyl phosphate, C8 to C30 alkyl ether phosphate or mixtures thereof, and a C14 to C30 fatty alcohol. Other anionic gel network forming surfactants may also be used.

The gel network thickener system preferably comprises at least one non-ionic surfactant selected from the group consisting of fatty alcohol polyoxyalkylene esters, alkyl polyoxyalkylene ethers which are derived from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

Representative examples of anionic surfactants include salts (such as alkaline salts, for example, sodium salts, ammonium salts, amine salts, amino alcohol salts and magnesium salts) of the following compounds: alkyl ether carboxylates, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates; alkyl succinates, alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyl methylaminopropionate; acyl isethionates, N-acyl taurates; acyl lactylates; carboxyalkyl ether of alkyl polyglucosides; alkyl lecithin derivatives. The alkyl or acyl radical of all of these various compounds, for example, comprises from about 8 to 30 carbon atoms, and the aryl radical, for example, is chosen from phenyl and benzyl groups.

Anionic surfactants include alkyl ether phosphates, alkyl ether sulphates, alkyl glyceryl sulphonates, N-acyl sarcosinates, N-acyl taurates, acyl lactylates and carboxyalkyl ether of alkyl polyglucosides. Yet more preferable surfactants are selected from alkyl ether phosphates having an average 1 to 20, 1 to 10 or 1 to 3 ethylene oxide units.

The gel network thickener system preferably comprises at least one cationic surfactant selected from quaternary ammonium salts or amido-amines having at least one fatty chain containing at least about 20 carbon atoms and mixture thereof.

The quaternary ammonium salts have general formula $N^+(R^1R^2R^3R^4)X^-$: wherein, $R^1$ is selected from linear and branched radicals comprising about 20 to 30 carbon atoms, $R^2$ is selected from linear and branched radicals comprising about 20 to 30 carbon atoms or the same group as radicals $R^3$ to $R^4$, the radicals $R^3$ to $R^4$, which can be identical or different, are selected from linear and branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein $X^-$ is an anion selected from halides, such as chloride, bromide and iodide) $(C_2\text{-}C_6)$alkyl sulphates, such as methyl sulphate, phosphates, alkyl and alkylaryl sulphonates, and anions derived from organic acids, such as acetate and lactate. The cationic surfactant is, for example, a behentrimonium chloride, behenamidopropyltrimonium methosulfate, stearamidopropyltrimonium chloride, arachidtrimonium chloride and mixtures thereof.

The amido-amine have general formula $R'^1$—CONH$(CH_2)_nNR'^2R'^3$: wherein, $R'^1$ is selected from linear and branched radicals comprising about 20 to 30 carbon atoms, the radicals $R'^2$ and $R'^3$, which can be identical or different, are selected from hydrogen, linear and branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein n is integer from 1 to 4. The amido-amine can be selected from, for example, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, and mixtures thereof.

In one preferred embodiment of the presently claimed invention, the surfactant which is used to form the gel network systems is selected from the group consisting of ceteareth-25, steareth-20, steareth-100, steareth-150, steareth-200 and mixtures thereof. These surfactants act as a co-emulsifier and stabilizer of the gel network system.

Those skilled in the art will recognize that gel network thickener systems usually have a complex structure of networked lamellar bi-layers and/or vesicles and sometimes crystals. These systems usually have creamy appearance and feel and are thus particularly desirable.

In one embodiment of the presently claimed invention, the hair colouring formulation may further comprise at least one anionic, cationic, nonionic, amphoteric, or zwitterionic polymer or mixtures thereof; antioxidants; penetrants; sequestrants; fragrances; dispersants; film-forming agents; ceramides; preserving agents; and opacifiers.

In a preferred embodiment of the presently claimed invention the suitable non-associative cross-linked polycarboxylic polymers for use herein can be selected, for example, from: (i) cross-linked acrylic acid homopolymers; or (ii) copolymers of acrylic or (meth)acrylic acid and of C1-C6 alkyl acrylate or (meth)acrylate. Such polymers are sold under the names Carbopol 980, 981, 954, 2984, 5984 by the company Noveon or Synthalen M, Synthalen L and Synthalen K by the company 3V Sigma, or Aculyn-33 by the company Rohm and Haas.

Polysaccharides may also be used, for example, glucans, modified and unmodified starches, amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and bio-polysaccharides, such as xanthan gums, gellan gums, welan gums, scleroglucans, succinoglycans and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums—Polysaccharides and their Derivatives", edited by Roy L. Whistler, Second Edition, published by Academic Press Inc.

The oxidizing composition of the presently claimed invention may be based on the same or similar (i.e. having the same ingredients but possibly at different level) formulation chassis as the tint component.

In one embodiment of the presently claimed invention, the colouring composition of the invention is obtained by mixing the tint composition and oxidizing composition. The tint composition comprises at least one alkalizing agent and a mixture of oxidative dyes. The oxidizing composition comprises the hydrogen peroxide. Such two component systems are commonly used in the art and each component is formulated so that the resulting mixture is a hair colouring composition according to the invention.

Packaging

In one embodiment of the presently claimed invention, before use, the tint and oxidizing compositions used in the invention are normally packaged separately from one another. The compositions may be packaged in separate primary packages such as plastic bottle, sachet or tube. The components, in particular each component of a two-component composition, may however be packaged separately but within a common secondary package such as a carton or in different compartment of an aerosol or foam bottle, as in known in the trade. A conditioning composition, which can be applied after rinsing of the hair colouring composition, may also be packaged in such secondary package. On the other hand, the different components of the invention, in particular the third component, may be sold separately from the other components.

Method of Hair Dying

Application of the hair colouring composition to the hair may be undertaken in several ways. Application of the hair colouring composition may take place on the whole head of hair of an end user. As used herein, the "whole head of hair" means that the hair all over the head from the root of the hair to the tip of the hair is included in the application process. By contrast, the application of the hair colouring composition may take place only on the root portion of the hair. The application to the root portion of the hair may still be over the entire head of the end user, but application of the hair colouring composition is applied only to the section of hair closest to the head (root portion), which is between about 0.01 mm to about 40 mm from the scalp of the head. After application to the root portion, product may be applied to the rest of the hair at a later stage to prevent over processing of the hair in the lengths and ends. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in an additional container. In the latter case, the conditioner can be mixed immediately before use and applied together with the other components, or the content of the additional container can be applied (after an optional rinse step) as a post-treatment immediately after the hair colouring composition.

According to one method for oxidatively colouring hair, the method comprises mixing a tint composition and an oxidizing composition and optionally a third component comprising a second non-ammonia alkalizing agent together to form a hair colouring composition, applying the hair colouring composition to the hair to form a treated hair surface, waiting for a period of 5-50 minutes, such as 20-35 minutes, and then removing the hair colouring composition from the treated hair surface through rinsing with water.

The methods of colouring hair also may further comprise working the hair colouring composition into the treated hair surface by hand or by a tool for a few minutes to ensure uniform application to the entire treated hair surface. The hair colouring composition remains on the treated hair surface while the end hair colour develops for a time period of 5 to 50 minutes to form oxidatively coloured hair.

The consumer then rinses his/her oxidatively coloured hair thoroughly with tap water and allows it to dry and/or styles the oxidatively coloured hair.

In one embodiment of the presently claimed invention, a method of treating hair with the composition preferably comprises the steps of:

a. providing a tint composition as described herein;
b. providing an oxidizing composition as described herein;
c. mixing the oxidizing composition and the tint composition to obtain a mixed hair colouring composition as described herein;
d. applying the mixed hair colouring composition for the oxidative dyeing of keratin fibres onto the hair;
e. leaving the composition on the hair for 5 to 50 minutes; and
f. subsequently rinsing the composition from the hair.

In one embodiment of the presently claimed invention, the hair colouring composition may be obtained by mixing immediately prior to use a tint composition and the oxidizing composition. A sufficient amount of the mixed colouring composition is applied to the hair, according to the hair abundance, generally from 20 to 250 grams depending on the amount of hair to be coloured. Upon such preparation, the colouring composition is applied to the hair to be dyed and remains in contact with the hair for an amount of time effective to dye the hair. Typically, the hair colouring composition is allowed to act on the hair from 5 to 50, preferably 10 to 40, preferably 20 to 35 minutes, at a temperature ranging from 15 to 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The hair colouring composition can be applied on hair via an applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse. The composition may be dispensed as a solid form to which water is added to generate the oxidant and form a thickened vehicle suitable for hair colouring. The invention is associated with one or more of the following advantages:

high lift of the hair
a wider range of desired colour shades for colouring the hair
low levels of damage of the hair
a pleasant odour profile while application to the hair
reduced levels of dye adducts
less off-tone In the following, there is provided a list of embodiments to further illustrate the present disclosure without intending to limit the disclosure to the specific embodiments listed below.

EMBODIMENTS

1. An oxidative hair colouring composition comprising
   a) 2-amino-1-propanol;
   b) at least one oxidizing agent;
   c) at least one oxidative primary dye precursor; and
   d) at least one oxidative coupler dye precursor.
2. The oxidative hair colouring composition according to embodiment 1, wherein the component a) is present in an amount in the range of ≥0.1 wt. % to ≤10.0 wt. %, based on the total weight of the oxidative hair colouring composition.
3. The oxidative hair colouring composition according to embodiment 1 or 2, wherein the component a) is present in an amount in the range of ≥0.1 wt. % to ≤7.0 wt. %, based on the total weight of the oxidative hair colouring composition.
4. The oxidative hair colouring composition according to embodiment 1 to 3, wherein the component a) is present in an amount in the range of ≥1.0 wt. % to ≤6.3 wt. %, based on the total weight of the oxidative hair colouring composition.
5. The oxidative hair colouring composition according to embodiments 1 to 4, wherein the component a) is present in an amount in the range of ≥1.0 wt. % to ≤2.5 wt. %, based on the total weight of the oxidative hair colouring composition.
6. The oxidative hair colouring composition according to embodiment 1 to 5, wherein b) the at least one oxidizing agent is hydrogen peroxide.
7. The oxidative hair colouring composition according to any one of embodiments 1 to 6, wherein the component b) is present in an amount in the range of ≥1.0 wt. % to ≤8.0 wt. %, based on the total weight of the oxidative hair colouring composition.
8. The oxidative hair colouring composition according to any one of embodiments 1 to 7, wherein the component b) is present in an amount in the range of ≤1.2 wt. % to ≤5.0 wt. %, based on the total weight of the oxidative hair colouring composition.
9. The oxidative hair colouring composition according to any one of embodiments 1 to 8, wherein the component c) the at least one oxidative primary dye precursor is selected from the group consisting of toluene-2,5-diamine, p-phenylenediamine, n-phenyl-p-phenylenediamine, N,N-bis(2-hydroxyethyl)-p-phenylenediamine, hydroxyethyl-p-phenylenediamine sulphate, hydroxypropyl bis(n-hydroxyethyl-p-phenylenediamine), 2-methoxymethyl-p-phenylenediamine, 2-chloro-p-phenylenediamine, p-aminophenol, p-methylaminophenol, 4-amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol 2,3-diaminodihydroxypyrazolopyrazolone dimethosulfonate, 4,5-diamino-1-hexylpyrazol, hydroxypropyl-p-phenylenediamine, dimethylpiperazinium aminopyrazolopyridine chloride hydrochloride, methylimidazoliumpropyl p-phenylenediamine, hydroxyethoxy aminopyrazolopyridine and salts thereof.
10. The oxidative hair colouring composition according to any one of embodiments 1 to 9, wherein c) the at least one oxidative primary dye precursor is selected from the group consisting of toluene-2,5-diamine, 2-methoxymethyl-p-phenylenediamine and salts thereof.
11. The oxidative hair colouring composition according to any one of embodiments 1 to 8, wherein d) the at least one oxidative coupler dye precursor is selected from the group consisting of resorcinol, 4-chlororesorcinol, 2-chlororesorcinol, 2-methylresorcinol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, hydroxybenzomorpholine, 2-amino-5-ethylphenol, 6-amino-m-cresol, 6-amino-o-cresol, 2,4-diaminophenoxyethanol, 2-amino-4-hydroxyethylaminoanisole, 1,3-bis-(2,4-diaminophenoxy)propane, 2,6-dihydroxyethylaminotoluenep, m-phenylenediamine, 2,4-diamino-1,5-di(2-hydroxyethoxybenzene, 1-naphthol, 2-methyl-1- naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindole, 6-hydroxyindole, dihydroxyindoline, phenyl methyl pyrazolone, 1,2,4-trihydroxybenzene, 5-((2-hydroxyethyl)amino)-1,3-benzodioxol, isatin, hydroquinone, 4-formyl-1-methylquinolinium-p-toluenesulfonate and salts thereof.

12. The oxidative hair colouring composition according to any one of embodiment 11, wherein d) the at least one oxidative coupler dye precursor is selected from the group consisting of resorcinol, 2-methylresorcinol, m-aminophenol, 2,4-diaminophenoxyethanol, 2-methyl-5-hydroxyethylaminophenol, 5-((2-hydroxyethyl)amino)-1,3-benzodioxol and salts thereof.

13. The oxidative hair colouring composition according to any one of embodiments 1 to 12 comprising;
   a) ≥1.0 wt. % to ≤3.0 wt. % 2-amino-1-propanol,
   b) ≥1.2 wt. % to ≤5.0 wt. % hydrogen peroxide,
   c) at least one primary dye precursor and
   d) at least one oxidative coupler dye precursor,
   wherein the wt. % are each based on the total weight of the oxidative hair colouring composition.

14. The oxidative hair colouring composition according to any one of embodiments 1 to 13 comprising:
   a) ≥1.0 wt. % to ≤2.5 wt. % 2-amino-1-propanol,
   b) ≥1.2 wt. % to ≤5.0 wt. % hydrogen peroxide,
   c) at least one primary dye precursor and
   d) at least one oxidative coupler dye precursor,
   wherein the wt. % are each based on the total weight of the oxidative hair colouring composition.

15. The oxidative hair colouring composition according to any one of embodiments 1 to 14, wherein the oxidative hair colouring composition has a pH in the range of ≥8.5 to ≤10.5.

16. The oxidative hair colouring composition according to any of embodiments 1 to 15, wherein the composition comprises at least one direct dye selected from the group consisting of Acid Yellow 1, Disperse Red 17, Basic Brown 17, Acid Black 1, Picramic acid, HC Red 13, N,N'-Bis(2-hydroxyethyl)-2-nitro-p-phenylenediamine, HC Blue 2, HC Yellow 4, HC Yellow 2, HC Orange 1, HC Red 1, HC Red 3, 4-Amino-3-nitrophenol, 3-Nitro-p-hydroxyethylaminophenol, 4-Nitrophenyl aminoethylurea, HC Red 10, HC Red 11, 2-Hydroxyethyl picramic acid, HC Blue 12, Hydroxyethyl-2-nitro-p-toluidine, HC Yellow 12, HC Yellow 7, 2-Chloro-6-(ethylamino)-4-nitrophenol, 2-Amino-6-Chloro-4-Nitrophenol, 4-Hydroxypropylamino-3-nitrophenol, HC Yellow 13, 2,6-Diamino-3-((pyridin-3-yl)azo)pyridine, Basic violet 2, Basic Red 51, HC Blue 16, Basic Orange 1, Basic Red 76, Basic Brown 16, Basic Yellow 57, CI14700, Acid Orange 7, FD&C Yellow 6, Acid Red 33, Acid Yellow 23, Acid Blue 9, Acid violet 9, Acid Red 92, Acid Yellow 3, 1-Amino-4-hydroxy-9,10-anthracendion, CI 60725, Acid violet 43, Disperse Violet 1, Carbon black, Disperse Black 9, Curry red, 2-Hydroxy-1,4-naphthoquinone, *Lawsonia inermis* Cera, *Indigofera tinctoria*, HC Blue 14, CI 42053, Acid Red 52, Acid Green 25, Disperse Blue 377, Pigment Red 57, HC Blue 15, Tetrabromphenol Blue, Anthocyanins, Chlorophyllin-Copper complex, Annatto, Natural Green 3, Betanin, Capsanthin, Basic Yellow 29 and combinations thereof.

17. The oxidative hair colouring composition according to any of embodiments 1 to 18, wherein the composition comprises at least one chelant selected from the group consisting of ethylenediamine tetraacetic acid (EDTA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), salts, derivatives, and mixtures thereof.

18. The oxidative hair colouring composition according to embodiment 17, wherein the at least one chelant is present in an amount from ≥0.20 wt. % to ≤1.5 wt. %, based on the total weight of the oxidative hair colouring composition.

19. The oxidative hair colouring composition according to any of embodiments 1 to 18, wherein the composition comprises at least one fatty substance selected from the group consisting of linear or branched, optionally cyclic, C6-C16 alkanes, non-silicone oils of animal, plant, mineral or synthetic origin, fatty alcohols, fatty acids, fatty acid esters and/or fatty alcohol esters, non-silicone waxes, silicones and mixtures thereof.

20. The oxidative hair colouring composition according embodiment 19, wherein the fatty alcohols are selected from the group consisting of cetyl alcohol, stearyl alcohol, cetostearyl alcohol, cetearyl alcohol, behenyl alcohols, and mixtures thereof.

21. The oxidative hair colouring composition according to embodiment 20, wherein the at least one fatty substance is present in an amount in the range of ≥2.0 wt. % to ≤70.0 wt. %, based on the total weight of the oxidative hair colouring composition.

22. The oxidative hair colouring composition according to any of embodiments 1 to 21, wherein the composition comprises at least one thickener or a gel network thickener system; selected from the group consisting of polymeric thickeners, mineral thickeners and organic thickeners and combinations thereof.

23. The oxidative hair colouring composition according to embodiment 22, wherein the at least one thickener is present in an amount in the range of ≥0.05 wt. % to ≤20 wt. %, based on the total weight of the oxidative hair colouring composition.

24. The oxidative hair colouring composition according to any of embodiments 1 to 23, wherein the composition comprises at least one non-ionic surfactant.

25. The oxidative hair colouring composition according to embodiment 24, wherein the at least one non-ionic surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

26. The oxidative hair colouring composition according to embodiment 25, wherein the alkyl polyoxyalkylene ethers are selected from the group consisting of steareth-20, steareth-100 and steareth-150.

27. The oxidative hair colouring composition according to any of embodiments 1 to 26, wherein the hair colouring formulation comprises a gel network thickener system formed from at least one surfactant and at least one fatty alcohol.
28. The oxidative hair colouring composition according to embodiment 27, wherein the at least one fatty alcohol is selected from the group consisting of cetyl alcohol, stearyl alcohol, cetostearyl alcohol, cetearyl alcohol, behenyl alcohols, and mixtures thereof the surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides.
29. The oxidative hair colouring composition according to embodiment 27, wherein the gel network system comprises a linear or branched C14 to C30 fatty alcohol in an amount in the range from ≥1.0 wt. % to ≤10.0 wt. %, preferably from ≥1.0 wt. % to ≤8.0 wt. %, based on the total weight of the oxidative hair colouring composition.
30. The oxidative hair colouring composition according to embodiment 27, wherein the at least one surfactant is at least one anionic, non-ionic, cationic or amphophilic surfactant or a combination thereof.
31. The oxidative hair colouring composition according to embodiment 30, wherein the at least one anionic surfactant is selected from the group consisting of C8 to C30 alkyl phosphates, C8 to C30 alkyl ether phosphates and mixtures thereof.
32. The oxidative hair colouring composition according to embodiment 30, wherein the at least one non-ionic surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylglucoamides, alkyl methyl sulfoxides and alkyl dimethyl phosphine oxides.
33. The oxidative hair colouring composition according to embodiment 30, wherein the at least one cationic surfactant is selected from the group consisting of quaternary ammonium salts, amido-amines having at least one fatty chain containing at least about 20 carbon atoms and mixture thereof.
34. The oxidative hair colouring composition according to any of embodiments 1 to 33, wherein the composition comprises a second alkalizing agent selected from the group consisting of 2-amino-1-butanol, ammonia and monoethanolamine.
35. The oxidative hair colouring composition according to embodiment 34, wherein the molar ratio of ammonia to 2-amino-1-propanol is in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.
36. The oxidative hair colouring composition according to embodiment 34, wherein the molar ratio of monoethanolamine to 2-amino-1-propanol is in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.
37. The oxidative hair colouring composition according to embodiment 34, wherein the molar ratio of 2-amino-1-butanol to 2-amino-1-propanol is in the range of 5.0:1.0 to 1.0:5.0, preferably in the range of 3.0:1.0 to 1.0:3.0, more preferably in the range of 2.0:1.0 to 1.0:2.0, most preferably in the range of 1.5:1.0 to 1.0:1.5.
38. A kit comprising;
    A) a tint composition comprising components a), c) and d) as defined in any one of embodiments 1 to 37 and
    B) an oxidative composition comprising component b) as defined any one of embodiments 1 to 37.
39. A method of treating hair comprises the steps of:
    a. providing a tint composition (A) as defined in any one of embodiments 1 to 37,
    b. providing an oxidative composition (B) as defined in any one of embodiments 1 to 37,
    c. mixing the tint composition and the oxidative composition to obtain a mixed hair colouring composition according to any one of embodiments 1 to 37,
    d. applying the hair colouring composition onto the hair;
    e. leaving the composition on the hair for a period from 5 to 50 minutes; and
    f. subsequently rinsing the composition from the hair.
40. The method for treating hair according to embodiment 39, wherein the tint composition (A) is mixed with the oxidative composition (B) in a weight ratio in the range of ≥3.0:1.0 to 1.0:3.5.
41. Use of 2-amino-1-propanol as an alkalizing agent in an oxidative hair colouring composition.

Examples

The following examples illustrate the formulations and performance results according to the presently claimed invention. These examples are not intended to be inclusive of all aspects of the subject matter disclosed herein, but rather to illustrate representative compositions and results. These examples are not intended to exclude equivalents and variations of the presently claimed invention, which are apparent to one skilled in the art.

In all below examples a series of tint compositions are created with the same molar level of alkalizing agents. The same molar level is used to ensure a consistent comparison between the materials.

Method of Measurements

1. Hair Damage Measurement Via FT-IR

Damage caused to the hair was assessed by a FT-IR (Fourier Transform Infrared) method, which was established to be suitable for studying the effects of keratin surface damage. Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M., Int. J. Cosmet. Sci., 19, 1-13 (1997)). In particular, these authors have shown that the method was suitable for quantifying the amount of cysteic acid. In general, the oxidation of cystine is thought to be a suitable marker by which to monitor the overall oxidation of the keratinous part of the fiber. Net, the measurement of cysteic acid units by FT-IR was commonly used.

Signori and Lewis (D. M., Int. J. Cosmet. Sci., 19, 1-13 (1997)) showed that FT-IR using a diamond Attenuated Total Internal Reflection (ATR) cell was a sensitive and reproducible way of measuring the cysteic acid content of single fibers and bundles. Hence, the method that was employed to measure the cysteic acid content of multiple fibre bundles and full hair switches, was based upon the FTIR diamond cell ATR method employed by Signori and Lewis (1997). The detailed description of the method for testing the different damage inhibitors follows thereafter:

A Perkin Elmer Spectrum® 1 Fourier Transform Infrared (FTIR) composition equipped with a diamond Attenuated Total Internal Reflection (ATR) cell was used to measure the cysteic acid concentration in mammalian or synthetic hair. In this method, hair switches of various sizes and colours were used. The switches were platted (~1 plait per cm) in order to minimize variations in surface area of contact between readings. The Oxidative hair Treatment Protocol described above was repeated for 5 cycles to mimic the behaviour of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check was performed using the monitor ratio mode of the instrument. As prescribed by Signori & Lewis in 1997, a normalized double derivative analysis routine was used. The original spectra was initially converted to absorbance, before being normalized to the 1450 $cm^{-1}$ band (the characteristic and invariant protein $CH_2$ stretch). This normalized absorbance was then twice derivatised using a 13-point averaging. The value of the 1450 $cm^{-1}$ normalized 2nd derivative of the absorbance at 1040 $cm^{-1}$ was taken as the relative concentration of cysteic acid. This figure was multiplied by $-1\times10^4$ to recast it into suitable units.

2. Colour Measurement Via Spectrophotometer

A Minolta spectrophotometer CM-2600d was used to measure the colour of the cured and dried hair tresses, five points on both the front and back sides, and the average D65 L*a*b values reported.

3. Adduct Determination Via HPLC Measurement

Instrumentation: A HPLC system Ultimate 3000 RSCL (Thermo Fisher), including Ultimate 3000 RS pump (high pressure gradient pump), Ultimate 3000 RS Diode Array detector, and Dionex Corona Veo RS Charged Aerosol Detector (=CAD) was used within the analysis. HPLC separations were performed on a reversed phase C18 HPLC column (e.g. Atlantis T3, 3.0 μm, 3.0×150 mm, Waters). All solvents were HPLC-MS grade. HPLC gradient was used with a flow of 0.4 ml/min, 15 μl injection volume, with the column at 40° C. (+1-2° C.). The gradient conditions used were as follows:

| Time (minutes): | 20 mM $NH_4$ HCOO | MeOH |
|---|---|---|
| 0 | 90 | 10 |
| 15 | 65 | 35 |
| 24 | 10 | 90 |
| 27 | 5 | 95 |
| 30 | 90 | 10 |
| 33 | 90 | 10 |

Detector signals recorded: UV-VIS (200-800 nm), MS (m/z=50-1000 amus, ESI in positive mode), and CAD. Compound identity was confirmed by MS and UV-VIS, quantification was typically done at 230-800 nm, and confirmed by Charged Aerosol Detection. Alternatively, within a given species, the MS was compared between test legs.

Tested Alkali Materials:

A series of alkali materials were tested to determine which gave the best overall performance. Table 1 shows the three alkali materials known within the area of hair colourants, and 2-amino-1-propanol as the new inventive alkali material.

TABLE 1

List of tested alkali material tested

| Compound | Structure | Comment |
|---|---|---|
| Ammonia | $NH_3$ | not within the scope of the presently claimed invention |
| Monoethanolamine (MEA) | 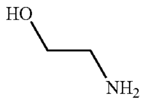 | not within the scope of the presently claimed invention |
| 2-amino-1-propanol (2A1P) | 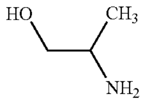 | |
| 2-amino-2-methyl-1-propanol (AMP) | 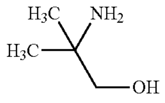 | not within the scope of the presently claimed invention |

Assessment of Overall Performance of 2-Amino-1-Propanol Comparing to Known Alkali Materials The overall performance of 2A1P was assessed versus the requirements of:

1. Being able to deliver low to no unpleasant odour (example 1),
2. Being able to deliver the same amount of hair bleaching or lift as the current standard non-ammonia alkali, monoethanolamine (MEA), with an acceptable hair damage (example 2)
3. Being able to reduce the amount of undesired adduct formation (example 3)
4. Being able to deliver a broader dye shade palette consumers desire by lowering dye adduct levels versus monoethanolamine (MEA) (example 4).

Example 1: Comparing Alkali "Odour" Performance

A series of tint compositions were created with the same molar level of the alkali under investigation, as shown in Table 2a. The same molar level was used to ensure a rigorous comparison between the materials. Table 2a shows the tint composition formulations in terms of weight percent of the different materials used.

Table 2b shows the oxidative composition in terms of weight percentage of the materials used. Table 2b ingredients were mixed with the tint composition given in Table 2a and provided ready to use oxidative hair colouring formulae.

TABLE 2a

Tint compositions with different alkali materials.

| Tint Ingredients | Composition 1A* (% w/w) | Composition 1B* (% w/w) | Composition 1C (% w/w) | Composition 1D* (% w/w) |
|---|---|---|---|---|
| DI water | q.s | q.s | q.s | q.s |
| Disodium EDTA (BASF) | 0.100 | 0.100 | 0.100 | 0.100 |
| Ascorbic acid (OSKAR BERG) | 0.300 | 0.300 | 0.300 | 0.300 |
| Sodium Sulfite (BCD CHEMIE) | 0.400 | 0.400 | 0.400 | 0.400 |
| Ammonia Solution (25%) (Brenntag GmbH) | 4.527 | | | |
| Monoethanolamine (MEA) (SASSOL) | | 4.066 | | |
| 2-Amino-1-propanol (2A1P) (Angus) | | | 5.000 | |
| 2-Amino-2-methyl-1-propanol (AMP) (Angus) | | | | 5.933 |
| Crème pre-mix formula | 40.000 | 40.000 | 40.000 | 40.000 |
| Cetearyl Alcohol (BASF) | (10.000) | (10.000) | (10.000) | (10.000) |
| Steareth-20 (CRODA) | (3.000) | (3.000) | (3.000) | (3.000) |
| DI Water | (27.000) | (27.000) | (27.000) | (27.000) |

q.s: quantity sufficient
*not within the scope of the presently claimed invention TABLE 2b Oxidative composition (1E) (6% Developer)

| Ingredients | Composition 1E (% w/w) |
|---|---|
| Water Purified (q.s) | q.s. |
| Salicylic Acid | 0.10 |
| Disodium Phosphate | 0.08 |
| Phosphoric Acid (85%) | 0.06 |
| Etidronic Acid | 0.01 |
| Hydrogen peroxide (50% Hydroxide peroxide Interox co-SO, SOLVAY) | 12 |
| Water Purified (q.s) | q.s. |
| Crème pre-mix formula | 20.00 |

TABLE 2b-continued

Oxidative composition (1E) (6% Developer)

| Ingredients | Composition 1E (% w/w) |
|---|---|
| Cetearyl Alcohol (BASF) | (5.00) |
| Steareth-20 (CRODA) | (1.50) |
| DI Water | (13.50) |

q.s: quantity sufficient

The formulations were prepared according to the following methods.

Crème pre-mix formula was a part of either the tint formulation or the oxidizing formulation. A crème pre-mix is created by combining together DI water (68.5%), cetearyl alcohol (25%) and Steareth-20 (6.5%). The mixture was heated to 80-85° C. to melt the waxes and surfactant with stirring. The composition was homogenized for 5 minutes and then cooling was started to reduce the product to room temperature. The resulting crème pre-mix was thick and used in the batches 1A-1D and also within the oxidizing composition 1E.

Tint Compositions:

The remaining components of the tint formula for each product were mixed together at room temperate with DI water. When all of the materials were dissolved, 40 wt. % of the crème pre-mix was added, and the mixture stirred until a uniform consistency was obtained. The products were then stored in aluminium tubes until used.

Oxidizing Compositions:

The remaining components were mixed together with the DI water at room temperature. When all of the materials were dissolved, 20 wt. % of the crème pre-mix was added, and the mixture stirred until a uniform consistency was obtained. The products were then stored in plastic bottles until used.

In the examples of the presently claimed invention either 6% or 9% oxidizing formula (Developer from the Wella Company) was used.

Sniff Testing Method for Comparing Alkali "Odour" Performance 10 g of tint compositions of 1A to 1D were mixed with 10 g of an oxidizing composition (Welloxon Perfect 6% Developer from the Wella Company) (tint and oxidizing compositions are mixed 1:1 in weight ratios) within a hair colouring bowl.

The 8 panellists were then asked to rate the odour of the mixed colouring composition on a scale of 0 (no strong or ammonia odour) through to 3 (very strong odour). The results are shown in table 3.

TABLE 3

Sniff test panellist results for comparing alkali "odour" Performance

| Example | Tint composition used to prepare colouring composition | Average Panellist score |
|---|---|---|
| 1a* | 1A | 1.5 |
| 1b* | 1B | 0 |
| 1c | 1C | 0 |
| 1d* | 1D | 0 |

*not within the scope of the presently claimed invention

The sniff test showed that the alkali materials used in examples 1b to 1d provided the low odour profile that consumers desire. Example 1a had a strong odour which was not preferred.

Example 2: Comparing Alkali "Lift Vs. Hair Damage" Performance

Within the following series of experiments, a series of alkali materials were tested for their performance for bleaching, lightening or "lifting" pigmented human hair and the associated damage performance. In all below examples a series of tint compositions was created with the same molar level of alkalizing agents. The same molar level was used to ensure a consistent comparison between the materials.

A Minolta spectrophotometer CM-2600d was used to measure the colour of hair tresses using the method described below to determine the L* value to provide a relative measure of lift. A Perkin Elmer Spectrum® 1 Fourier Transform Infrared (FTIR) was equipped with a diamond Attenuated Total Internal Reflection (ATR) cell was used to measure the cysteic acid concentration as a measure of the damage on the hair tress according to the method as described above.

In this series of examples, the same tint compositions given in Table 2a (1A-1D) are used.

Lift Vs Hair Damage Performance Testing Method

The tint compositions (1A-1D) are also used within testing to determine the hair lifting or bleaching performance, and the amount of damage the colouring compositions created on the hair. The following protocol was used to assess the performance of each colouring composition.

1. 2 Level 5 hair tresses (Kerling details) were used to test each colouring composition.
2. 1 part of each tint composition (1A to 1 D) was mixed with 1 part of oxidizing composition (Welloxon Perfect 6%) and then applied and worked throughout the hair tresses with a brush. 4 g of product was applied to each 1 g tress.
3. The tresses were placed into a 30° C. oven for 30 minutes for the bleaching process to occur.
4. The tresses were then removed from the oven and rinsed in water, 4 L $min^{-1}$ at a temperature of 37+−2° C. for 2 minutes
5. The tresses were then dried with a hair drier.

This procedure was repeated 5 times and the resulting hair tresses were then measured for lift via L*a*b value and damage ATR FT-IR using the methods described above. The lift and hair damage results are captured in the table 4.

TABLE 4

Lift vs. Hair Damage Test Results after 5 colouring cycles

| Example | | L* value[2] | Statistical Groups[1] | | | FT-IR damage | Statistical Groups[1] |
|---|---|---|---|---|---|---|---|
| 2a* | 1A (Ammonia) | 40.0 | A | | | 81.7 | A |
| 2b* | 1B (MEA) | 38.9 | | B | | 83.9 | A |
| 2c | 1C (2A1P) | 38.8 | | B | | 82.1 | A |
| 2d* | 1D (AMP) | 37.8 | | | C | 82.4 | A |

*not within the scope of the presently claimed invention

[1]Tukey-Kramer HSD Comparison of all pairs with alpha = 0.05. Letters not connected by the same letter are significantly different.

[2]initial tress before any colour cycles is L* = 26.3

The results show that lift performance falls into three groups. Those with the highest level of lift; by use of ammonia (example 2a), those with high lift; by use of monoethanolamine (example 2b) or 2-amino-1-propanol (example 2c) and those with low lift; by use of 2-amino-2-methyl-1-propanol (example 2d). The level of damage assessed via ATR FT-IR was not statistically different for the different alkali materials.

The results presented via Table 3 and 4 show that the combined effect of providing a pleasant odour while delivering a wide range of potential shades by high lift at an acceptable hair damage can only be achieved by use of monoethanolamine or 2-amino-1-propanol.

Example 3: Adduct Formation

TABLE 5

Tint compositions with different alkali media.

| Tint Ingredients | Composition 2A* (% w/w) | Composition 2B* (% w/w) | Composition 2C (% w/w) |
|---|---|---|---|
| DI water | q.s | q.s | q.s |
| Disodium EDTA | 0.100 | 0.100 | 0.100 |
| Ascorbic acid | 0.300 | 0.300 | 0.300 |
| Sodium Sulfite | 0.400 | 0.400 | 0.400 |
| 2-methoxymethyl-p-phenyl enediamine - Primary dye (DRAGON CHEMICALS) | 0.951 | 0.951 | 0.951 |
| Resorcinol - Coupler dye (ACETO) | 0.688 | 0.688 | 0.688 |
| Ammonia Solution (25%) | 4.527 | | |
| Monoethanolamine | | 4.066 | |
| 2-amino-1-propanol | | | 5.000 |
| Crème pre-mix | 40.000 | 40.000 | 40.000 |
| (Cetearyl Alcohol) | (10.000) | (10.000) | (10.000) |
| (Steareth-20) | (3.000) | (3.000) | (3.000) |
| (DI Water) | (27.000) | (27.000) | (27.000) |

*not within the scope of the presently claimed invention

The tint compositions were prepared in a similar way to the compositions used in the lift/damage study. The components were mixed together until fully dissolved, and then the crème pre-mix was added and the product mixed until being homogenous.

The tint compositions were created with the same molar level of alkalizing agents. The same molar level was used to ensure a consistent comparison between the materials. The prepared tint compositions were then mixed with the oxidizing composition (1E) as described above.

Method of Applying Hair Colouring Formulation to Hair

All products and equipment for the hair dye-out were equilibrated to 30° C. in a circulation oven overnight. Level 5 hair tresses (Kerling International Haarfabrik GmbH, Backnang, Germany) were preselected by weight. Tresses weighing in total 900 mg (+/−10 mg) were found to have 630 mg of free hair, accessible to the mixed crème colouring composition in the following dye-out process.

Equal weights (approximately 4 g each) of tint composition (2A-2C) and oxidizing composition (1E) were mixed in a bowl using a dye-out brush, this mixture was referred to as the mixed colouring composition as claimed in the presently claimed invention.

Approximately 1260 mg (+/−20 mg) of colouring composition was applied to the free hair portion of a tress (weight ratio colouring composition:hair~2:1) and the colour developed at 30° C. for 30 minutes in a 30° C. circulation oven. After colour development and removal from the oven, excess colouring composition was squeezed out from the tress by hand, wearing nitrile gloves.

Table 6 below shows the formation of regular dye products as well as undesired mono and/or di-adduct formation. These regular dyes and adduct formations are than quantified by HPLC-MS method as described above and the result being shared in Table 7 below.

TABLE 7

Adduct formation amount in the examples of using tint compositions 2A-2C with an oxidizing composition to make the colouring composition

| Example | Tint composition used in colouring composition | Regular* | (Mono-adduct) | (Di-adduct) |
|---|---|---|---|---|
| 3a* | 2A (Ammonia) | 100% | 0% | 0% |
| 3b* | 2B (Monoethanolamine) | 39.3% | 20.2% | 40.5% |
| 3c | 2C (2-amino-1-propanol) | 73.7% | 7.6% | 18.7% |

*not within the scope of the presently claimed invention

Amounts in colouring composition are percentage of the total products formed for a given alkalizer.

The results in table 7 clearly show that 2-amino-1-propanol (example 3c) produced far lower levels of the adducts in the mixed colouring composition compared to monoethanolamine (example 3b). This reduced level of off-tone coloured species formed and enabled higher levels of dyes to be used within the shading process. As expected, example 3a produced no adducts. The results in Table 7, clearly shows that the amount of regular dye products formed by use of 2A1P (example 3c) is increased by almost 50% compared to the use of MEA (example 3b).

TABLE 6

List of formed dye and dye adducts

| | Species | Structure |
|---|---|---|
| (Formed in Ammonia System - 2A tint composition) | Regular Dye Product (and its isomers) | 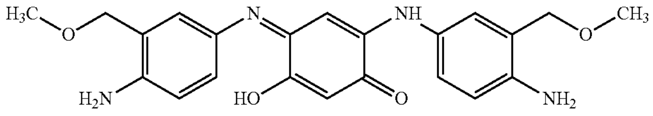 |
| (Formed in MEA System - 2B tint composition) | Regular | Same as ammonia system |
| | Mono-Adduct (and its isomers) | 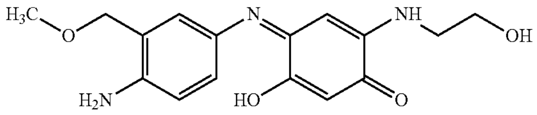 [SMILES: COCc1cc(/N=C2/C=C(NCCO)C(=O)C=C2O)ccc1N] |
| | Di-Adduct | 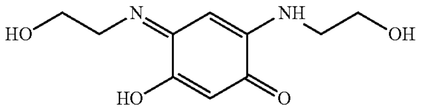 [SMILES: O=C1C=C(O)/C(=N\CCO)C=C1NCCO] |
| (Formed in 2A1P System - 2C tint composition) | Regular | Same as ammonia system |
| | Mono-Adduct (and its isomers) | 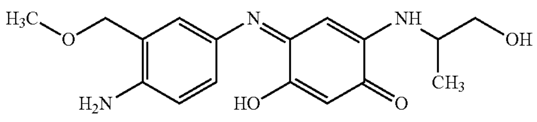 [SMILES: COCc1cc(/N=C2/C=C(NC(C)CO)C(=O)C=C2O)ccc1N] |
| | Di-Adduct (and its isomers) | 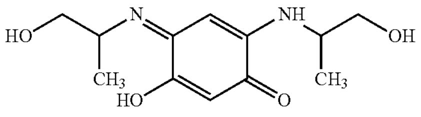 [SMILES: CC(CO)/N=C1/C=C(NC(C)CO)C(=O)C=C1O] |

Example 4: Shades Enabled by 2-Amino-1-Propanol Compared to MEA

In all below examples a series of tint compositions was created with the same molar level of alkalizing agents. The same molar level is used to ensure a consistent comparison between the materials.

The tint compositions (4A-4D) were mixed with a 6% hydrogen peroxide oxidizing composition (1E) and applied to hair to provide a dark brown colour. The pH of the mixed formulation was around 9.5 for all mixtures.

The first two examples 4A and 4B containing dye combinations with MEA produced levels of dye adducts that could not be release for consumer usage. However, when the same dye formulations were transformed into the inventive examples 4C and 4D (with 2A1P), the dye shades were formed and the level of dye adducts was sufficiently low to enable their use by consumers. As a result, the dye shades that could not be formulated with MEA (examples 4A, 4B) were successfully formulated in the 2A1P formulations (examples 4C and 4D).

TABLE 8

Comparison of Different Dye Shade Formation by using MEA and 2-amino-1-propanol

| Tint Ingredients | Ex. 4A* (% w/w) | Ex. 4B* (% w/w) | Ex. 4C (% w/w) | Ex. 4D (% w/w) |
|---|---|---|---|---|
| DI water | q.s | q.s | q.s | q.s |
| Disodium EDTA | 0.100 | 0.100 | 0.100 | 0.100 |
| Ascorbic acid | 0.300 | 0.300 | 0.300 | 0.300 |
| Sodium Sulfite | 0.400 | 0.400 | 0.400 | 0.400 |
| Primary dyes | | | | |
| 2,5-toluenediamine sulfate | 1.900 | | 1.900 | |
| 2-methoxymethyl-p-phenylenediamine | | 1.75 | | 1.75 |
| Coupler dyes | | | | |
| Resorcinol | 0.700 | 1.000 | 0.700 | 1.000 |
| m-Aminophenol | 0.250 | 0.175 | 0.250 | 0.175 |
| 2,4-diaminophenoxyethanol 2HCl | 0.050 | 0.010 | 0.050 | 0.010 |
| 2-Methyl-5-Hydroxyethylaminophenol | | 0.010 | | 0.010 |
| 5-((2-hydroxyethyl)amino)-1,3-benzodioxol | | 0.110 | | 0.110 |
| Alkalisers | | | | |
| MEA | 4.066 | 4.066 | | |
| 2-amino-1-propanol | | | 5.000 | 5.000 |
| Crème pre-mix | 40.000 | 40.000 | 40.000 | 40.000 |
| Cetearyl Alcohol | (10.000) | (10.000) | (10.000) | (10.000) |
| Steareth-20 | (3.000) | (3.000) | (3.000) | (3.000) |
| DI Water | (27.000) | (27.000) | (27.000) | (27.000) |
| Dye Shade Formation Results | Fail | Fail | Pass | Pass |

*not within the scope of the presently claimed invention

Example 5: Hair Colouring Formulations with Different Levels of 2-Amino-1-Propanol A series of tint compositions were prepared analogous to composition 1C, but with varying levels of 2-amino-1-propanol. These tint compositions were mixed 1:1 with 9% Welloxon Perfect (oxidizing composition) and then applied to Level 4 hair tresses (from the same hair supplier described above) using the method previously described. The level of 2-amino-1-propanol within the tint compositions was varied such that the mixed colouring composition had a resulting alkali level between 0.1 wt. % and 10.0 wt. %. After 30 minutes of development time at 30° C. the product was rinsed and the hair dried.

The starting and final hair colour was measured to assess the lifting performance. Table 9 shows the resulting lift, measured as dL.

TABLE 9

Lift performance at different 2-amino-1-propanol levels

| Example | 2-amino-1-propanol level (% w/w) in mixed hair colouring composition | dL = (L*final − L*initial) |
|---|---|---|
| 5A | 0.10 | 1.3 |
| 5B | 0.50 | 1.3 |
| 5C | 1.00 | 2.5 |
| 5D | 1.50 | 2.5 |
| 5E | 2.50 | 3.7 |
| 5F | 6.25 | 5.0 |
| 5G | 10.00 | 5.2 |

Initial tress before any colour cycles is L* initial = 26.3

The results of the level study with 2-amino-1-propanol show that at low levels of 2-amino-1-propanol the level of lightening of the hair tresses (5A and 5B) was very low. The dL values were below 2 which is typically considered to be the limit of what can be observed by a consumer. Such low levels of lightening make it hard to deliver a broad range of shades, as it is hard to blend in grey hairs within some lift occurring. This is therefore not a desirable level of performance for a hair colouring composition.

When the level of 2-amino-1-propanol was 1.00 wt. % or higher (5C to 5G) the dL is higher than 2 and noticeable by a consumer. This makes it possible to start to create shades which can blend in grey. At the highest levels of alkali (G), there was a minimal difference between 6.25 wt. % (SF) and 10.00 wt. % (5G). The additional alkali makes no significant difference to the performance of the product, but only increases the pH. This higher pH led to increased irritation potential of the colouring composition.

Example 6: Hair Colouring Formulations of Mixed Alkali Systems

The tint compositions 6A-6E contain combinations of 2A1P with a second alkalizing agent.

In all below examples a series of tint compositions was created with the same molar level of alkalizing agents. The same molar level was used to ensure a consistent comparison between the materials.

TABLE 10

Example tint compositions showing the impact of mixed alkali systems.

| Tint Ingredient | Ex. 6A* (% w/w) | Ex. 6B* (% w/w) | Ex. 6C (% w/w) | Ex. 6D (% w/w) | Ex. 6E (% w/w) |
|---|---|---|---|---|---|
| DI water | q.s | q.s | q.s | q.s | q.s |
| Disodium EDTA | 0.100 | 0.100 | 0.100 | 0.100 | 0.100 |
| Ascorbic acid | 0.300 | 0.300 | 0.300 | 0.300 | 0.300 |
| Sodium Sulfite | 0.400 | 0.400 | 0.400 | 0.400 | 0.400 |
| 2-methoxymethyl-p-phenylenediamine Primary dye | 0.951 | 0.951 | 0.951 | 0.951 | 0.951 |
| m-Aminophenol Coupler dye | 0.608 | 0.608 | 0.608 | 0.608 | 0.608 |
| Ammonia Solution (25%) | 4.527 | | | 2.264 | |
| Monoethanolamine | | 4.066 | | | 2.033 |
| 2-amino-1-propanol | | | 5.000 | 2.500 | 2.500 |
| Crème pre-mix | 40.000 | 40.000 | 40.000 | 40.000 | 40.000 |
| (Cetearyl Alcohol) | (10.000) | (10.000) | (10.000) | (10.000) | (10.000) |
| (Steareth-20) | (3.000) | (3.000) | (3.000) | (3.000) | (3.000) |
| (DI Water) | (27.000) | (27.000) | (27.000) | (27.000) | (27.000) |

*not within the scope of the presently claimed invention

The tint compositions were mixed in a ratio of 1:1 with an oxidizing composition (1E/6% developer).

The mixed alkali colouring compositions using tint compositions 60 and 6E with oxidizing compositions showed lower levels of adducts versus the single alkali compositions (6B and 6C). With the mixture of ammonia and 2-amino-1-propanol (60D), the level of 2A1P dye adducts was almost halved in comparison to composition 6C. The combination with ammonia had an additional advantage in that the products had a reduced odour profile compared to the ammonia alone product. With the mixture of MEA and 2-amino-1-propanol (6E), the level of MEA based dye adduct was reduced by a third, and the level of 2-amino-1-propanol based dye adduct was reduced by more than half compared to compositions 6B and 6C. The mixed systems were able to further reduce the adduct levels, even though the molar level of the total alkali was kept constant.

Examples 7: Shades Enabled by Alternative Mixed Alkali Systems

The tint compositions 7A to 7F provided a dark brown colour, when mixed with 6% hydrogen peroxide oxidizing composition and applied to hair. The final pH of the mixture was around 9.5 for all examples.

The two examples 7A and 70 which use different dye combinations with MEA produced levels of dye adducts that could not be release for consumer usage. However, when the same dye formulations were transformed into the inventive formulations 7B, 7C, 7E and 7F, the desired dye shades were formed and the level of dye adducts was sufficiently low to enable their use by consumers. As a result, the dye shades that could not be formulated in MEA formulations (7A and 7D) were successfully formulated in the mixed alkali examples (7B, 7C, 7E and 7F).

In all below examples a series of tint compositions was created with the same molar level of alkalizing agents (single alkalizing agent or the combination reaches out the same molar level). The same molar level was used to ensure a consistent comparison between the materials

TABLE 11

Mixed alkali formulations to deliver more shades

| | 7A* | 7B | 7C | 7D* | 7E | 7F |
|---|---|---|---|---|---|---|
| DI water | q.s | q.s | q.s | q.s | q.s | q.s |
| Disodium EDTA | 0.10 | 0.10 | 0.10 | 0.10 | 0.10 | 0.10 |
| Ascorbic acid | 0.30 | 0.30 | 0.30 | 0.30 | 0.30 | 0.30 |
| Sodium Sulfite | 0.40 | 0.40 | 0.40 | 0.40 | 0.40 | 0.40 |
| Primary Dyes | | | | | | |
| 2,5-toluenediamine sulfate | | | | 2.75 | 2.75 | 2.75 |
| 2-methoxymethyl-p-phenylenediamine | 1.92 | 1.92 | 1.92 | | | |
| Coupler dyes | | | | | | |
| Resorcinol | 1.00 | 1.00 | 1.00 | 1.000 | 1.000 | 1.000 |
| m-Aminophenol | 0.20 | 0.20 | 0.20 | 0.400 | 0.400 | 0.400 |
| 2,4-diaminophenoxyethanol 2HCl | 0.05 | 0.05 | 0.05 | | | |
| 2-Methyl-5-Hydroxyethylaminophenol | 0.05 | 0.05 | 0.05 | | | |
| 5-((2-hydroxyethyl)amino)-1,3-benzodioxol | 0.30 | 0.30 | 0.30 | | | |

TABLE 11-continued

| Mixed alkali formulations to deliver more shades | | | | | | |
|---|---|---|---|---|---|---|
| | 7A* | 7B | 7C | 7D* | 7E | 7F |
| Alkalisers | | | | | | |
| Ammonia Solution | | | 2.26 | | | 2.26 |
| MEA | 4.07 | 1.50 | | 4.07 | 1.50 | |
| 2A1P | | 3.10 | 2.50 | | 3.10 | 2.50 |
| Crème pre-mix | 40.00 | 40.00 | 40.00 | 40.00 | 40.00 | 40.00 |
| (Cetearyl Alcohol) | (10.00) | (10.00) | (10.00) | (10.00) | (10.00) | (10.00) |
| (Steareth-20) | (3.00) | (3.00) | (3.00) | (3.00) | (3.00) | (3.00) |
| (DI Water) | (27.00) | (27.00) | (27.00) | (27.00) | (27.00) | (27.00) |
| Dye Shade Formation Results | Fail | Pass | Pass | Fail | Pass | Pass |

*not within the scope of the presently claimed invention

The potential palette of shades was increased even further by using a combination of 2A1P and MEA and/or ammonia.

The invention claimed is:

1. An oxidative hair colouring composition comprising
 a) an alkalizer selected from the group consisting of 2-amino-1-propanol, 2-amino-1-propanol with ammonia and 2-amino-1-propanol with monoethanolamine and any combination thereof;
 b) at least one oxidizing agent;
 c) at least one oxidative primary dye precursor; and
 d) at least one oxidative coupler dye precursor.

2. The oxidative hair colouring composition according to claim 1, wherein the component a) is present in an amount in the range of ≥0.1 wt. % to ≤10.0 wt. % based on the total weight of the oxidative hair colouring composition.

3. The oxidative hair colouring composition according to claim 1, wherein b) the at least one oxidizing agent is hydrogen peroxide.

4. The oxidative hair colouring composition according to claim 1, wherein the component b) is present in an amount in the range of ≥1.0 wt. % to ≤8.0 wt. %, based on the total weight of the oxidative hair colouring composition.

5. The oxidative hair colouring composition according to claim 1, wherein c) the at least one oxidative primary dye precursor is selected from the group consisting of toluene-2,5-diamine, p-phenylenediamine, n-phenyl-p-phenylenediamine, N,N-bis(2-hydroxyethyl)-p-phenylenediamine, hydroxyethyl-p-phenylenediamine sulphate, hydroxypropyl bis(n-hydroxyethyl-p-phenylenediamine), 2-methoxymethyl-p-phenylenediamine, 2-chloro-p-phenylenediamine, p-aminophenol, p-methylaminophenol, 4amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol, 2,3-diaminodihydroxypyrazolopyrazolone dimethosulfonate, 4,5-diamino-1-hexylpyrazol, hydroxypropyl-p-phenylenediamine, dimethylpiperazinium aminopyrazolopyridine chloride hydrochloride, methylimidazoliumpropyl p-phenylenediamine, hydroxyethoxy aminopyrazolopyridine and salts thereof.

6. The oxidative hair colouring composition according to claim 1, wherein d) the at least one oxidative coupler dye precursor is selected from the group consisting of rescorcinol, 4-chlororesorcinol, 2-chlororesorcinol, 2-methylresorcinol, maminophenol, 4-amino-2-hydroxytoluene, 2-methyl-5-hydroxyethylaminophenol, 3-amino-2,6dimethylphenol, 3-amino-2,4-dichlorophenol, 5-amino-6-chloro-o-cresol, 5-amino-4-chloro-ocresol, hydroxybenzomorpholine, 2-amino-5-ethylphenol, 6-amino-m-cresol, 6-amino-ocresol, 2,4-diaminophenoxyethanol, 2-amino-4-hydroxyethylaminoanisole, 1,3-bis-(2,4diaminophenoxy) propane, 2,6-dihydroxyethylaminotoluenep, m-phenylenediamine, 2,4diamino-1,5-di(2-hydroxyethoxy-benzene, 1-naphthol, 2-methyl-1-naphthol, 1,5naphthalenediol, 2,7-naphthalenediol, 1-acetoxy-2-methylnaphthalene, 2,6-dihydroxy-3,4dimethylpyridine, 2,6-dimethoxy-3,5-pyridinediamine, 3-amino-6-methoxy-2-(methylamino) pyridine, 2-amino-3-hydroxypyridine, 2,6-diaminopyridine, dihydroxyindole, 6hydroxyindole, dihydroxyindoline, phenyl methyl pyrazolone, 1,2,4-trihydroxybenzene, 5-((2hydroxyethyl)amino)-1,3-benzodioxol, isatin, hydroquinone, 4-formyl-1-methylquinoliniump-toluenesulfonate and salts thereof.

7. The oxidative hair colouring composition according to claim 1, wherein the oxidative hair colouring composition has a pH in the range of ≥8.5 to ≤10.5.

8. The oxidative hair colouring composition according to claim 1, wherein the composition comprises at least one chelant selected from the group consisting of ethylenediamine tetraacetic acid (EDTA), ethylenediamine-N,N'-disuccinic acid (EDDS), ethylenediamine-N,N'-diglutaric acid (EDDG), 2-hydroxypropylenediamine-N,N'disuccinic acid (HPDDS), glycinamide-N,N'-disuccinic acid (GADS), ethylenediamine-N—N'bis(ortho-hydroxyphenyl acetic acid) (EDDHA), dimethyl glucamine (DMG), salts, derivatives, and mixtures thereof.

9. The oxidative hair colouring composition according to claim 8, wherein the at least one chelant is present in an amount in the range from ≥0.20 wt. % to ≤1.5 wt. %, based on the total weight of the oxidative hair colouring composition.

10. The oxidative hair colouring composition according to claim 1, wherein the composition comprises at least one fatty substance selected from the group consisting of linear or branched, optionally cyclic, C6-C16 alkanes, non-silicone oils of animal, plant, mineral or synthetic origin, fatty alcohols, fatty acids, fatty acid esters, fatty alcohol esters, non-silicone waxes, silicones, and mixtures thereof.

11. The oxidative hair colouring composition according to claim 10, wherein the at least one fatty substance is present in an amount in the range of ≥2.0 wt. % to ≤70.0 wt. %, based on the total weight of the oxidative hair colouring composition.

12. The oxidative hair colouring composition according to claim 1, wherein the composition comprises at least one thickener selected from the group consisting of polymeric thickeners, mineral thickeners, organic thickeners, a gel network thickener system and combinations thereof.

13. The oxidative hair colouring composition according to claim 12, wherein the at least one thickener is present in an amount in the range of ≥0.5 wt. % to ≤20 wt. %, based on the total weight of the oxidative hair colouring composition.

14. The oxidative hair colouring composition according to claim 1, wherein the composition comprises at least one non-ionic surfactant is selected from the group consisting of fatty alcohol polyoxyalkylene esters, alkyl polyoxyalkylene ethers which are derived from C1-C6-alcohols or from C7-C30-fatty alcohols, alkylaryl alcohol polyoxyethylene ethers, alkoxylated animal fats, alkoxylated animal oils, plant fats, plant oils, glycerol esters, alkylphenol alkoxylates, fatty amine alkoxylates, fatty acid amide alkoxylates, and fatty acid diethanolamide alkoxylates, sugar surfactants, sorbitol esters, polyoxyethylene sorbitan fatty acid esters, alkyl polyglycosides, N-alkylgluconamides, alkyl methyl sulfoxides and alkyl dimethyl phosphine oxides.

15. The oxidative hair colouring composition according to claim 1, wherein the alkalizing agent is 2-amino-1-propanol with ammonia, or 2-amino-1-propanol with monoethanolamine.

16. The oxidative hair colouring composition according to claim 15, wherein the molar ratio of ammonia to 2-amino-1-propanol is in the range of 5.0:1.0 to 1.0:5.0.

17. The oxidative hair colouring composition according to claim 15, wherein the molar ratio of monoethanolamine to 2-amino-1-propanol is in the range of 5.0:1.0 to 1.0:5.0.

18. The oxidative hair colouring composition according to claim 1, wherein the alkalizing agent is 2-amino-1-propanol.

19. A kit comprising

A) a tint composition comprising components a), c) and d) as defined in claim 1 and B) an oxidative composition comprising component b) as defined in claim 3.

20. A method of treating hair comprising the steps of:

a. providing a tint composition (A) comprising components a), c) and d) as defined in claim 1, b. providing an oxidative composition (B) comprising component b) as defined in claim 3, c. mixing the tint composition (A) and the oxidative composition (B) to obtain a mixed hair colouring composition according to claim 1, d. applying the hair colouring composition onto the hair;

e. leaving the composition on the hair for a period in the range from ≥5 to ≤50 minutes; and f. subsequently rinsing the composition from the hair.

21. The oxidative hair colouring composition according to claim 1 which produces a reduced amount of mono and di adducts of the primary dye precursor and coupler dye precursor relative to the amount of mono and di adducts produced by a composition of the oxidizing agent b), the oxidative primary dye precursor c), the oxidative coupler dye precursor d), and monoethanolamine alone as the alkalizer.

22. The oxidative hair colouring composition according to claim 1 which produces a reduced ammonia odor profile compared with a composition of the oxidizing agent b), the oxidative primary dye precursor c), the oxidative coupler dye precursor d), and ammonia alone as the alkalizer.

* * * * *